(12) United States Patent
Jeong et al.

(10) Patent No.: US 11,549,927 B2
(45) Date of Patent: Jan. 10, 2023

(54) METHOD AND ELECTRONIC DEVICE FOR CORRECTING AND GENERATING DATA RELATED TO OUTSIDE AIR ON BASIS OF MOVEMENT

(71) Applicant: Samsung Electronics Co., Ltd., Gyeonggi-do (KR)

(72) Inventors: Daeung Jeong, Gyeonggi-do (KR); Donguk Kwak, Gyeonggi-do (KR); Minho Park, Gyeonggi-do (KR); Hyuncheol Park, Gyeonggi-do (KR); Sunggun Bae, Gyeonggi-do (KR); Ikjoo Byun, Gyeonggi-do (KR); Hyejung Seo, Gyeonggi-do (KR); Daeyong Lee, Gyeonggi-do (KR); Seunggoo Lee, Gyeonggi-do (KR); Taeho Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 281 days.

(21) Appl. No.: 16/959,189

(22) PCT Filed: Jan. 11, 2019

(86) PCT No.: PCT/KR2019/000460
§ 371 (c)(1),
(2) Date: Jun. 30, 2020

(87) PCT Pub. No.: WO2019/139409
PCT Pub. Date: Jul. 18, 2019

(65) Prior Publication Data
US 2020/0400634 A1    Dec. 24, 2020

(30) Foreign Application Priority Data
Jan. 12, 2018  (KR) .......................... 10-2018-0004637

(51) Int. Cl.
*G01N 33/00*        (2006.01)
*G01P 13/00*        (2006.01)
(Continued)

(52) U.S. Cl.
CPC .......... *G01N 33/0062* (2013.01); *G01P 13/00* (2013.01); *G06F 1/1656* (2013.01); *G06F 3/14* (2013.01); *G06F 3/16* (2013.01)

(58) Field of Classification Search
CPC .............. G01N 33/0062; G01N 33/00; G01N 33/0006; G01P 13/00; G06F 1/1656;
(Continued)

(56) References Cited

U.S. PATENT DOCUMENTS

| 2006/0053862 | A1 | 3/2006 | Mayer et al. |
| 2012/0095643 | A1* | 4/2012 | Bose ...................... B60K 37/00 715/744 |

(Continued)

FOREIGN PATENT DOCUMENTS

| KR | 10-2015-0051070 A | 5/2015 |
| KR | 10-2016-0143373 A | 12/2016 |

(Continued)

*Primary Examiner* — Dinh Nguyen
(74) *Attorney, Agent, or Firm* — Cha & Reiter, LLC

(57) ABSTRACT

According to various embodiments of the disclosure, an electronic device comprising a gas sensor, a motion sensor, a processor, wherein the processor is configured to acquire data related to air outside the electronic device by using the gas sensor, identify a movement of the electronic device by using the motion sensor while acquiring the data, correct, in case that the movement of the electronic device satisfies a designated condition, at least partial data in an interval in which a movement satisfying the designated condition continues, among the data; and produce information related to quality of the air, at least based on the data, the at least partial data of which has been corrected.
Other embodiments may possible.

13 Claims, 9 Drawing Sheets

(51) Int. Cl.
*G06F 1/16* (2006.01)
*G06F 3/14* (2006.01)
*G06F 3/16* (2006.01)

(58) Field of Classification Search
CPC ............ G06F 3/14; G06F 3/16; G06F 1/1684; H04M 1/725; H04M 1/72454; H04M 2250/12
See application file for complete search history.

(56) References Cited

U.S. PATENT DOCUMENTS

| | | |
|---|---|---|
| 2015/0123984 A1 | 5/2015 | Kim et al. |
| 2016/0360384 A1 | 12/2016 | Park et al. |
| 2017/0199588 A1 | 7/2017 | Ahn et al. |
| 2017/0241843 A1 | 8/2017 | Jeon et al. |
| 2017/0318135 A1* | 11/2017 | Han .................. H04M 1/72454 |
| 2018/0299417 A1 | 10/2018 | Cha et al. |

FOREIGN PATENT DOCUMENTS

| | | |
|---|---|---|
| KR | 10-2017-0055216 A | 5/2017 |
| KR | 10-2017-0084558 A | 7/2017 |
| KR | 10-2017-0099157 A | 8/2017 |

* cited by examiner

METHOD AND ELECTRONIC DEVICE FOR CORRECTING AND GENERATING DATA RELATED TO OUTSIDE AIR ON BASIS OF MOVEMENT

CROSS REFERENCE TO RELATED APPLICATIONS

This application is a National Phase Entry of PCT International Application No. PCT/KR2019/000460, which was filed on Jan. 11, 2019, and claims a priority to Korean Patent Application No. 10-2018-0004637, which was filed on Jan. 12, 2018, the contents of which are incorporated herein by reference.

TECHNICAL FIELD

Various embodiments of the disclosure relate to a method for correcting and producing data related to outside air, based on a movement, and an electronic device therefor.

BACKGROUND ART

Gas sensors are installed and used at various places to monitor hazardous materials and pollutants in the atmosphere/environment. Gas sensors refer to elements which sense a specific chemical material contained in a gas, convert the concentration thereof into an electric signal, and output the same. There are various kinds of gas sensors according to the type of sensing. For example, gas sensors may be implemented in a type such that a change in the material characteristics of a solid resulting from adsorption or reaction of a gas is used, in a type such that combustion heat is used, in a type that an electrochemical reaction is used, or in a type such that physical characteristics are used.

Gas sensors may be mounted not only on fixed devices (for example, air purifiers, air conditioners, and indoor attached devices), but also on mobile electronic devices (for example, smartphones, laptop computers, and wearable devices).

DISCLOSURE OF INVENTION

Technical Problem

When a gas sensor mounted on a mobile electronic device measures the quality of ambient air, an air flow resulting from a movement of the user holding or wearing the mobile electronic device (for example, if the user walks while holding a smartphone by hand, or if the user swings arms while wearing a watch-type wearable device on a wrist) may cause an error in the value related to the measured air quality.

An electronic device according to various embodiments of the disclosure may determine whether or not the electronic device makes a movement based on data measured by a motion sensor, when monitoring the quality of ambient air by using a gas sensor, and may correct the sensor value measured by the gas sensor in the interval in which a movement has occurred, thereby providing an accurate sensor value from the gas sensor.

Solution to Problem

According to various embodiments of the disclosure, an electronic device comprising a gas sensor, a motion sensor, a processor, wherein the processor is configured to acquire data related to air outside the electronic device by using the gas sensor, identify a movement of the electronic device by using the motion sensor while acquiring the data, correct, in case that the movement of the electronic device satisfies a designated condition, at least partial data in an interval in which a movement satisfying the designated condition continues, among the data; and produce information related to quality of the air, at least based on the data, the at least partial data of which has been corrected.

According to various embodiments of the disclosure, a method for correcting and producing data related to ambient air of an electronic device, the method comprising: acquiring a first sensor value related to ambient air of the electronic device from a gas sensor, identifying a movement of the electronic device based on a second sensor value measured from a motion sensor while acquiring the first sensor value, correcting, in case that the movement of the electronic device satisfies a designated condition, at least partial data in an interval in which a movement satisfying the designated condition continues, among the first sensor value; and producing information related to quality of air, based on the first sensor value, the at least partial data of which has been corrected.

Advantageous Effects of Invention

According to various embodiments of the disclosure, a measurement error resulting from a movement of an electronic device may be prevented by reflecting whether or not the electronic device makes a movement when measuring the quality of ambient air.

According to various embodiments of the disclosure, the quality of ambient air is measured more accurately, and the user is accordingly provided with air quality measurement information, thereby advantageously preventing the user from erroneously recognizing the air quality.

MODE FOR THE INVENTION

Figure 1:
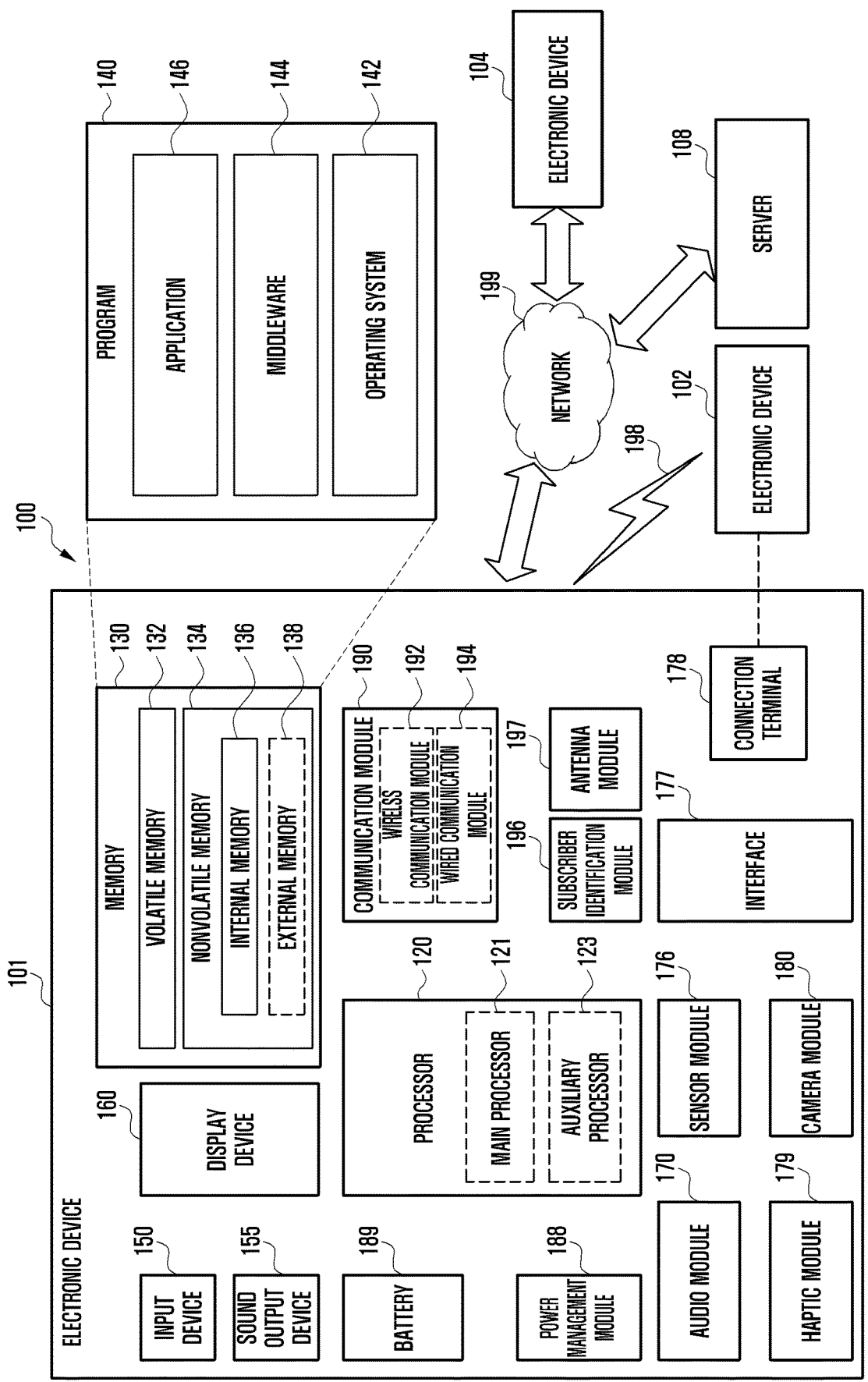
FIG. 1 is a block diagram illustrating an electronic device in a network environment 100 according to various embodiments.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. The processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other.

The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
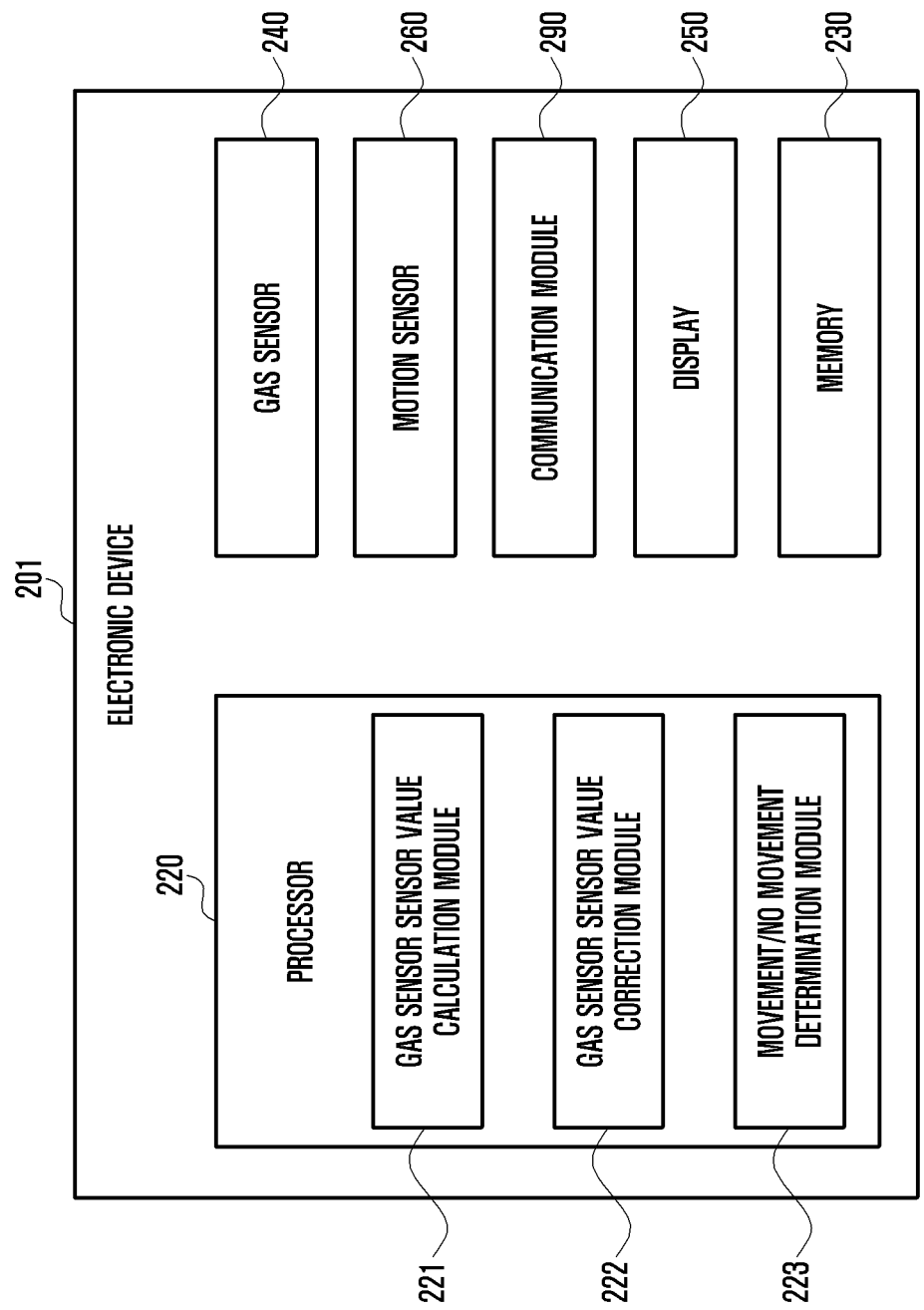
FIG. 2 illustrates an electronic device according to an embodiment of the disclosure.

FIG. 2 illustrates an electronic device according to an embodiment of the disclosure.

Referring to FIG. 2, the electronic device 201 (for example, 101 in FIG. 1) may include a processor 220 (for example, processor 120 in FIG. 1), a memory 230 (for example, memory 130 in FIG. 1), a gas sensor 240 (for example, sensor module 176 in FIG. 1), a display 250 (for example, display device 160 in FIG. 1), a motion sensor 260 (for example, sensor module 176 in FIG. 1), or a communication module 290 (for example, communication module 190 in FIG. 1). The electronic device 201 may further include a housing, and components of the electronic device 201 may be seated inside the housing or positioned on the housing.

The memory 230 according to an embodiment may store at least one piece of data (for example, sensor value or position information) measured by the gas sensor 240, the motion sensor 260, or the communication module 290. The memory 230 may store gas sensor measurement data corrected by the processor 220.

The gas sensor 240 according to an embodiment may sense a gas in the air outside the electronic device 201, and may collect data in order to determine the condition to sense a gas or to configure a measurement profile. The gas sensor 240 may acquire data (for example, sensor value) continuously or periodically, and may deliver the acquired data to the processor 220. The electronic device 201 according to an embodiment may include at least one gas sensor 240. The gas sensor 240 may include at least one of a semiconductor sensor, a ceramic humidity/temperature sensor, a piezoelectric sensor, a catalytic combustion sensor, a solid electrolyte sensor, an electrochemical sensor, and an infrared absorption sensor.

The display 250 (for example, display device 160 in FIG. 1) according to an embodiment may display at least one piece of data produced by the processor 220. For example, the display 250 may display notification information related to gas measurement information.

The motion sensor 260 according to an embodiment may collect data in order to sense the amount of change resulting from a movement of the electronic device 201. The motion sensor 260 may acquire data (for example, sensor value) continuously or periodically, and may deliver the acquired data to the processor 220.

The motion sensor 260 according to an embodiment may include at least one of an acceleration sensor configured to measure the acceleration of the electronic device 201, a gyro sensor capable of measuring the angular velocity of the electronic device 201, a magnetic sensor (for example, terrestrial magnetism sensor or compass sensor) capable of measuring the terrestrial magnetism, a barometer sensor capable of measuring an atmospheric pressure change and/or atmospheric pressure, a grip sensor, and a wearing detection sensor. The wearing detection sensor may be at least one of an optics-based sensor (including a light emitter and a light receiver), an electrode-based sensor, and a capacitance-type sensor. For example, the processor 220 may determine whether or not the user wears the electronic device (for example, watch-type wearable device) based on data measured by the wearing detection sensor.

The communication module 290 according to an embodiment may include, for example, at least one of a cellular module, a Wi-Fi module, a Bluetooth module, a GNSS module, an NFC module, and an RF module. The communication module 290 may acquire position information of the electronic device. For example, the GNSS module may output position information such as longitude, latitude, altitude, GPS speed, and GPS heading during a movement of the electronic device. The GNSS module may acquire time information together with three-dimensional speed information, in addition to the position of latitude, longitude, and altitude.

The processor 220 according to an embodiment may control the overall operation of the electronic device 201. The processor 220 may be electrically connected to the memory 230, the gas sensor 240, the display 250, the motion sensor 260, and the communication module 290.

The processor 220 according to an embodiment may process data measured by the gas sensor 240 and the motion sensor 260, and may control the display 250 so as to display the processed data or may control the output module (for example, speaker (for example, sound output device 155 in FIG. 1)) so as to output the processed data.

The processor 220 according to an embodiment may acquire sensing data related to ambient air from the gas sensor 240 or acquire sensing data related to the movement of the electronic device from the motion sensor 250. The processor 220 may monitor a sensor value measured from the gas sensor 240 or the motion sensor 250. The processor 220 may determine whether or not the electronic device 201 moves, based on a sensor value acquired by the motion sensor 260, while monitoring a sensor value of the gas sensor 240 in order to measure the quality of ambient air. If the electronic device 201 makes a movement that satisfies a designated condition, the processor 220 may correct at least a part of the sensor value measured from the gas sensor 240 according to the designated condition. The designated condition, as used herein, may be at least one of a condition that the movement of the electronic device 201 is equal to or larger than a threshold movement value or a condition that the time for which the movement of the electronic device is equal to or larger than the threshold movement value is equal to or larger than a threshold time value.

According to an embodiment, if the electronic device 201 includes a grip sensor or a wearing detection sensor, the processor 220 may determine whether or not the user is holding the electronic device (for example, smartphone), based on data measured by the grip sensor or the wearing detection sensor. If it is determined that the movement of the electronic device 201 in the holding state is equal to or larger than a designated threshold movement value, the processor 220 may correct the gas sensor value measured in the interval in which the movement of the electronic device 201 corresponds to the threshold movement value or at the timepoint of movement.

For example, if the electronic device 201 makes a movement that satisfies the condition that the movement thereof will be equal to or larger than a threshold movement value, the processor 220 may identify the length (or time) of the interval in which the movement of the electronic device 201 is equal to or larger than the threshold movement value, and may make a correction such that the sensor value measured by the gas sensor 240 in the identified movement interval is ignored or deleted.

As another example, if the condition that the movement of the electronic device 201 will be equal to or larger than a threshold movement value is satisfied, the processor 220 may delete the sensor value measured by the gas sensor 240 in the movement interval in which the electronic device 201 satisfies the condition, and may replace the sensor value of the gas sensor 240 by using preceding/following data measured adjacent to the interval of movement of the electronic device 201 according to the flow of time, or may replace the same with a data value of the gas sensor received from an external electronic device (for example, electronic device 102 in FIG. 1).

The processor 220 according to an embodiment may produce air quality measurement information by using a monitored sensor value of the gas sensor 240 or a corrected sensor value thereof, and may control the produced air quality measurement information to be provided to the user or to be transmitted to another electronic device (for example, electronic device 102 or 197 or server 108 in FIG. 1).

The processor 220 according to an embodiment may include a gas sensor sensor value calculation module 221, a gas sensor sensor value correction module 222, and a movement/no movement determination module 223. The gas sensor sensor value calculation module 221 may process and/or calculate sensing data acquired from the gas sensor 240. The movement/no movement determination module 223 may determine whether or not the electronic device 201 moves, or the degree of movement thereof, based on sensing data received from the motion sensor 260. For example, the movement/no movement determination module 223 may determine whether the electronic device 201 is in a stationary state or in a moving state (for example, walking or running), based on data measured by the motion sensor 260.

The gas sensor sensor value correction module 222 may correct a sensor value measured by the gas sensor sensor value calculation module 221 if it is determined by the movement/no movement determination module 223 that the electronic device is moving, and that the sensor value measured from the motion sensor 260 is equal to or larger than a configured threshold movement value. For example, the gas sensor sensor value correction module 222 may correct a sensor value of the gas sensor measured in a movement interval, if it is determined that the movement of the electronic device is equal to or larger than a designated threshold movement value.

According to an embodiment, the gas sensor sensor value correction module 222 may control a gas sensor value measured at a timepoint at which a movement occurred or in an interval in which the movement occurred so as to be ignored or deleted.

According to another embodiment, the gas sensor sensor value correction module 222 may replace a gas sensor value measured at a timepoint at which a movement occurred or in an interval in which the movement occurred, based on a gas sensor value measured immediately before/after the timepoint or interval in which the movement occurred.

According to another embodiment, the gas sensor sensor value correction module 222 may receive data measured by an external electronic device adjacent to a timepoint or an interval in which a movement occurred, and may substitute the received data for the gas sensor value measured at the timepoint at which the movement occurred or in the interval in which the movement occurred. The data measured by the external electronic device, that is, the ambient air measurement value, may include at least one of a value measured by the external electronic device at a time including at least a part of the timepoint or interval in which a movement of the electronic device 201 occurred, a value measured by an external electronic device (for example, electronic device 102 in FIG. 1) existing in a position close to the electronic device 201 (or within a configured distance), and a value measured when the movement of the external electronic device (for example, electronic device 102 in FIG. 1) is in a stationary state or is below a configured threshold value.

The processor 220 according to an embodiment may transmit a gas sensor value measured via the gas sensor sensor value calculation module 221 to an external electronic device (for example, electronic device 102 or 197 or server 108 in FIG. 1) via the communication module 290.

Additionally, the processor 220 according to an embodiment may transmit a movement sensor value measured via the gas sensor sensor value calculation module 221 and/or position information acquired via the communication module 290 to an external electronic device (for example, electronic device 102 or 197 or server 108 in FIG. 1) together with a gas sensor value.

Figure 3:
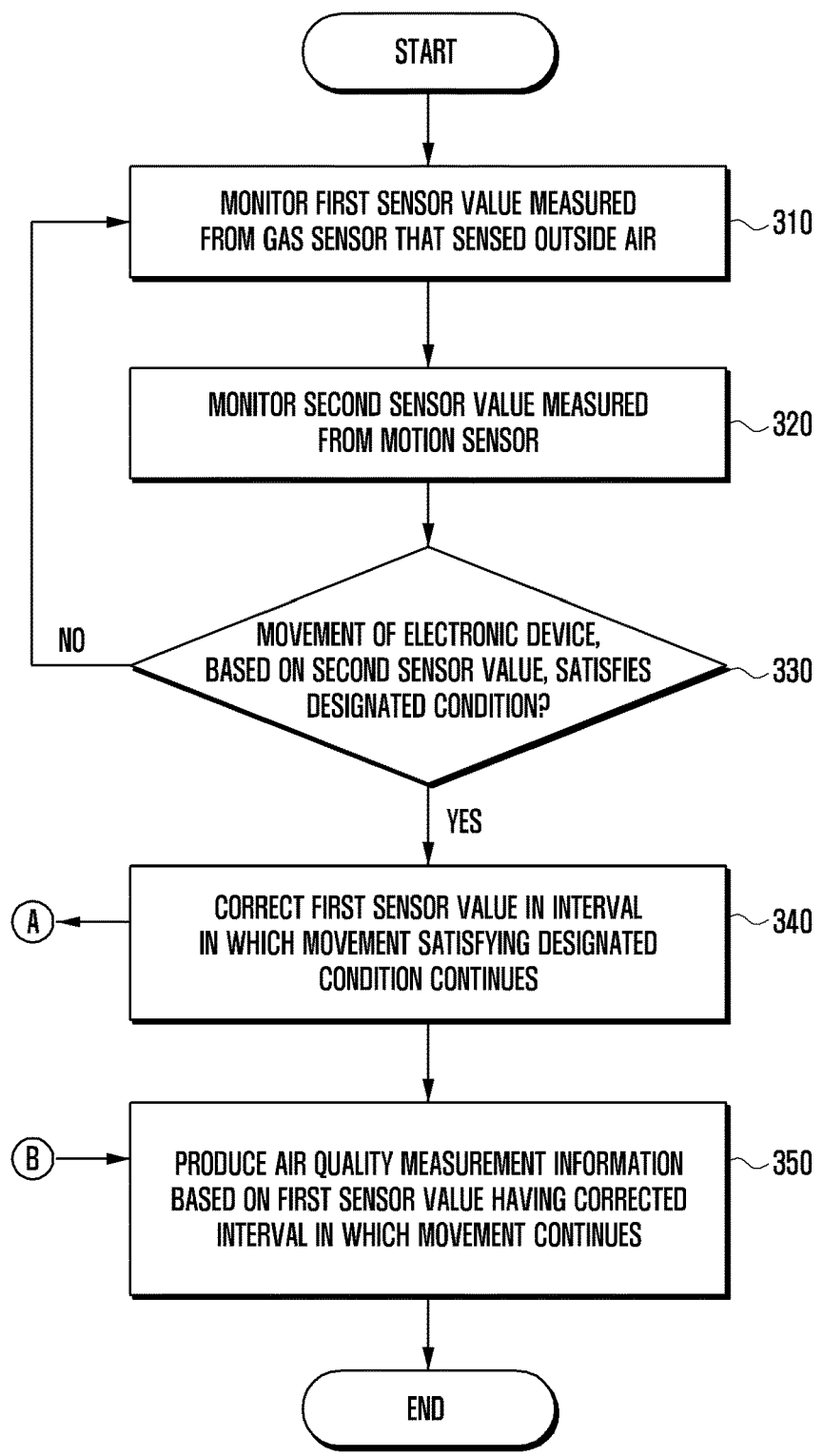
FIG. 3 illustrates a method for measuring a gas by an electronic device having a gas sensor according to an embodiment of the disclosure.

FIG. 3 illustrates a method for measuring a gas by an electronic device having a gas sensor according to an embodiment of the disclosure.

Referring to FIG. 3, the processor (for example, processor 120 in FIG. 1 or processor 220 in FIG. 2) of the electronic device 201 according to an embodiment of the disclosure may monitor a first sensor value measured from a gas sensor 240 configured to sense air quality in operation 310. The processor 120 or 220 may control the gas sensor 240 so as to measure the quality of air near the electronic device 201 periodically or continuously. Alternatively, the processor 120 or 220 may control the gas sensor 240 so as to sense ambient air from the gas sensor 240 in response to a user input requesting air measurement.

In operation 320, the processor 120 or 220 may monitor a second sensor value acquired based on sensing data of the motion sensor 260.

Operations 310 and 320, although illustrated successively for convenience of description, are not limited thereto, and the processor 120 or 220 may assign tasks to monitoring of the gas sensor 240 and monitoring of the motion sensor 260, respectively, and control the same so as to operate in a parallel manner.

In operation 330, the processor 120 or 220 may determine whether or not the movement of the electronic device 201 satisfies a designated condition while monitoring the second sensor value measured from the motion sensor 260. The processor 120 or 220 may determine whether the electronic device 201 is in a stationary state or in a movement state, based on the second sensor value measured from the motion sensor 260. According to an embodiment, the processor 120 or 220 may determine the movement state based on at least one of a threshold movement value and a threshold time value concerning a movement, which are designated with regard to the second sensor value measured from the motion sensor 260.

For example, the processor 120 or 220 may determine, as a result of comparing the second sensor value with a threshold movement value, that the electronic device 201 is in a movement state if the second sensor value is equal to or larger than the threshold movement value, and may determine that the electronic device 201 is in a stationary state if the second sensor value is less than the threshold movement value.

As another example, the processor 120 or 220 may determine that the electronic device 201 is in a movement state if the second sensor value in an interval in which the movement is equal to or larger than a threshold movement value is maintained for a threshold time value or longer, and may determine that the electronic device 201 is in a stationary state if the second sensor value does not exceed the threshold time value.

Although not illustrated in the drawings, the processor 120 or 220 may further include, according to an embodiment, an additional operation of determining, while monitoring a first sensor value measured from the gas sensor 240, whether or not the interval in which the first sensor value measured by the gas sensor exceeds a gas threshold value, or whether or not the interval in which the first sensor value changes is maintained for a designated time. If the gas measurement value measured from the gas sensor satisfies the designated condition, the processor 120 or 220 may proceed to operation 330. However, this is omissible.

In operation 340, if the movement of the electronic device 201 satisfies a designated condition, based on the second sensor value, the processor 120 or 220 may identify the interval (for example, interval t) in which a movement satisfying the designated condition continues, and may correct the first sensor value in the continuous interval.

According to an embodiment, the processor 120 or 220 may ignore or delete data of the first sensor value measured in the interval in which a movement satisfying the designated condition continues, and may correct the first sensor value such that the data in the continuous interval is not used to produce air quality measurement information.

According to an embodiment, the processor 120 or 220 may delete data of the first sensor value measured in the interval in which the movement satisfying the designated condition continues, and may correct the first sensor value in the continuous interval by using preceding/following data adjacent to the continuous interval according to the flow of time.

According to an embodiment, the processor 120 or 220 may replace data of the first sensor value measured in the interval in which the movement satisfying the designated condition continues with a data value of a gas sensor received from another electronic device (for example, electronic device 102 or 197 or server 108 in FIG. 1), thereby correcting the same. Operation 340 of correcting the interval in which the movement continues will be described later in detail with reference to FIG. 4 or FIG. 5.

In operation 350, the processor 120 or 220 may produce electronic device 201 ambient air quality measurement information based on the first sensor value after having the corrected interval in which the movement continues.

According to an embodiment, additionally, the processor 120 or 220 may simultaneously or selectively perform an operation of providing, as a notification, the air quality measurement information produced based on the first sensor value having the corrected interval in which the movement continues via the display 250 (for example, display device 160 in FIG. 1) or the audio module (for example, sound output device 155 (for example, speaker) in FIG. 1) or transmitting the same to an external electronic device (for example, electronic device 102 or 197 or server 108 in FIG. 1) via the communication module 190.

Meanwhile, if it is determined in operation 330, based on the second sensor value measured from the motion sensor 260, that the movement of the electronic device 201 does not satisfy the designated condition, the processor 120 or 220 may proceed to operation 310 and return to the operation of monitoring the first sensor value measured from the gas sensor 240.

Although not illustrated in the drawings, according to various embodiments, the processor 120 or 220 may monitor the first sensor value measured from the gas sensor 240 and produce air quality measurement information based on the first sensor value. If the air quality is changed, based on the amount of change of the first sensor value, the processor 120 or 220 may simultaneously or selectively perform an operation of providing, as a notification, the produced air quality measurement information via the display 250 (for example, display device 160 in FIG. 1) or the audio module 170 (or sound output device 155 (for example, speaker) in FIG. 1) or transmitting the same to an external electronic device (for example, electronic device 102 or 197 or server 108 in FIG. 1) via the communication module 190.

Figure 4:
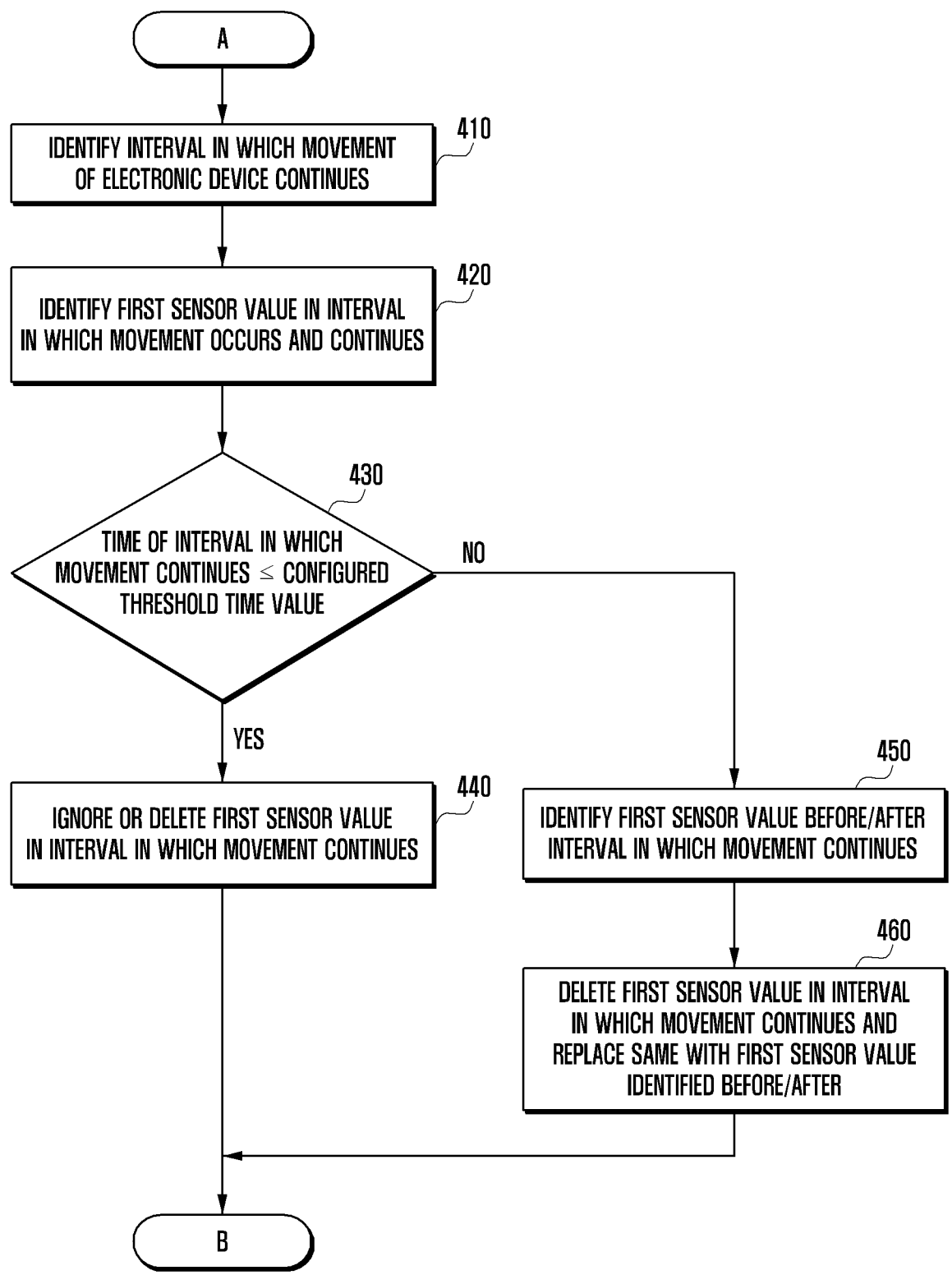
FIG. 4 illustrates a method for measuring a gas by an electronic device according to an embodiment of the disclosure.

FIG. 4 illustrates a method for measuring a gas by an electronic device according to an embodiment of the disclosure. FIG. 4 illustrates an example of specific operations regarding operation 340 in FIG. 3.

Specific operations regarding operation 340 in FIG. 3 according to an embodiment of the disclosure will be described with reference to FIG. 4. In operation 410, if the movement of the electronic device 201 satisfies a designated condition, based on a second sensor value, the processor (for example, processor 120 in FIG. 1 or processor 220 in FIG. 2) of the electronic device 201 may identify the interval in which the movement of the electronic device 201 occurred. The interval in which the movement of the electronic device 201 satisfying the designated condition continues may be identified based on time or click information, but is not limited thereto.

In operation 420, the processor 120 or 220 may identify a first sensor value in the interval in which the movement continues. In operation 430, the processor 120 or 220 may compare the time of the interval in which the movement continues with a designated threshold time value. If the time of the interval in which the movement continues is less than the designated threshold time value, the processor 120 or 220 may control the first sensor value in the interval in which the movement occurs and continues to be ignored or deleted, in operation 440. For example, if the electronic device 201 has made an instantaneous movement, the processor 120 or 220 may detect the amount of change in the movement of the electronic device, which is less than the threshold time value. In this case, the electronic device 201 may ignore the gas sensor value measured at the time less than the threshold time value, thereby preventing a measurement error resulting from the instantaneous movement. That is, the processor 120 or 220 may ignore or delete the first sensor value measured in the interval in which the movement continues such that, even if the first sensor value changes in the interval in which the movement continues, the processor 120 or 220 may ignore the same and monitor the first sensor value or produce air quality measurement information.

In operation 450, the processor 120 or 220 may compare the time of the interval in which the movement satisfying the condition continues with a designated threshold time value and, if the time of the continuous interval is equal to or larger than the threshold time value, may identify the first sensor value measured before/after the interval in which the movement continues.

In operation 460, the processor 120 or 220 may substitute the first sensor value measured immediately before/after the interval in which the movement continues for the first sensor value in the continuous interval, thereby correcting the same.

For example, if the time of the interval in which the movement satisfying the condition continues is too long to be ignored, the processor 120 or 220 may identify time information adjacent to the continuous interval and may identify a first sensor value measured at a time immediately before and/or after the interval in which the movement continues. Thereafter, the processor 120 or 220 may delete the first sensor value of the interval in which the movement continues and may replace the deleted first sensor value in the interval with the first sensor value measured at the time immediately before and/or after the interval in which the movement continues, thereby connecting first sensor values sensed from the gas sensor 240.

After correcting the first sensor value in the interval in which the movement continues, the processor 120 or 220 may proceed to operation 350 in FIG. 3 and produce electronic device 201 ambient air quality measurement information based on the first sensor value having the corrected interval in which the movement continues.

Figure 5:
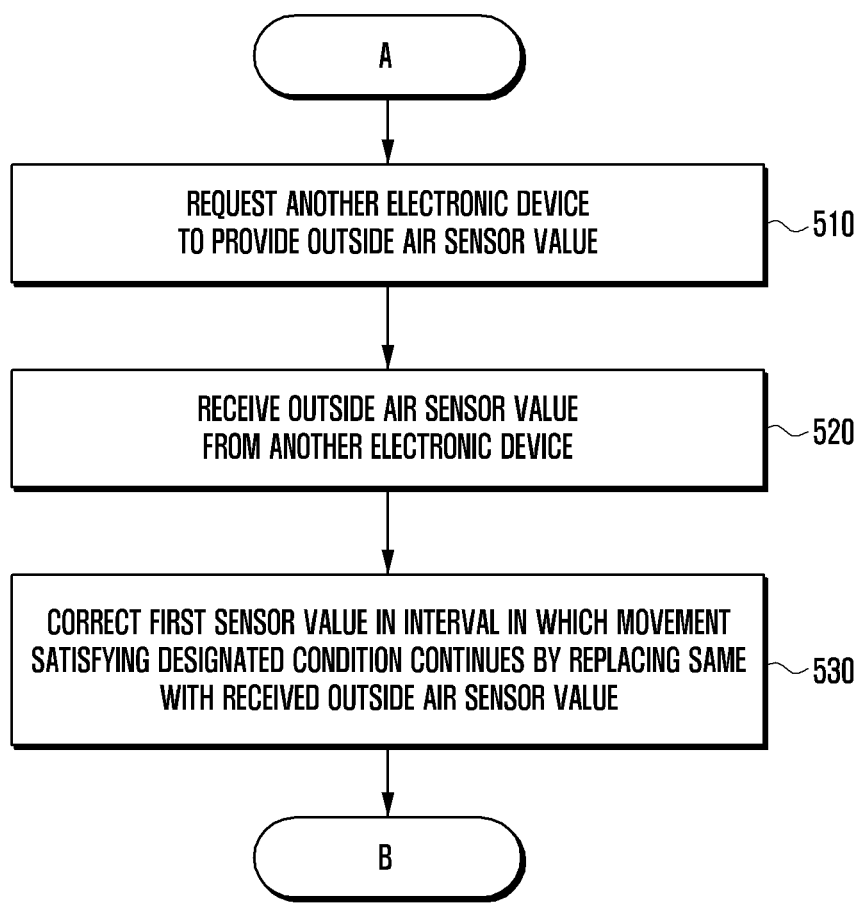
FIG. 5 illustrates a method for measuring a gas by an electronic device according to an embodiment of the disclosure.

FIG. 5 illustrates a method for measuring a gas by an electronic device according to an embodiment of the disclosure. FIG. 5 illustrates another example of specific operations regarding operation 340 in FIG. 3.

Specific operations regarding operation 340 in FIG. 3 according to another embodiment of the disclosure will be described with reference to FIG. 5. In operation 510, if the movement of the electronic device 201 satisfies a designated condition, based on a second sensor value, the processor (for example, processor 120 in FIG. 1 or processor 220 in FIG. 2) of the electronic device 201 may control the communication module 290 so as to send a request for an ambient air measurement value to another electronic device (for example, electronic device 102 or 197 or server 108 in FIG. 1). The designated condition, as used herein, may be at least one of a condition that the movement of the electronic device 201 will be equal to or larger than a threshold movement value or a condition that the time for which the movement of the electronic device 201 is equal to or larger than the threshold movement value is equal to or larger than a threshold time value.

For example, the processor 120 or 220 may request at least one of time information regarding the interval in which a movement of the electronic device satisfying a designated condition continues, based on a second sensor value measured from the motion sensor 260, and information regarding the current position thereof.

According to an embodiment, the processor 120 or 220 may send a request for an air measurement value to another electronic device (for example, electronic device 102 or 197 in FIG. 1) included within a designated distance (or range) from the position thereof, or may send a request for an air measurement value to a server (for example, server 108 in FIG. 1) that manages air quality information in an integrated manner.

In operation 520, the processor 120 or 220 may receive an ambient air measurement value from another electronic device 102, 108, or 197 via the communication module 290. For example, the air measurement value received from another electronic device 102, 108, or 197 may include at least one of a value measured by another electronic device 102, 108, or 197 at a time including at least a part of a continuous interval in which the movement of the electronic device 201 satisfies a designated condition, a value measured by another electronic device 102, 108, or 197 positioned close to the electronic device 201 or within a designated distance therefrom, and a value measured when the movement of another electronic device 102, 108, or 197 is in a stationary state or less than a designated threshold value.

In operation 530, the processor 120 or 220 may correct the first sensor value in the interval in which a movement satisfying the designated condition continues by replacing the same with the received ambient air measurement value.

After correcting the first sensor value in the interval in which the movement satisfying the designated condition continues by replacing the same with the ambient air measurement value received from another electronic device 102, 108, or 197, the processor 120 or 220 may procced to operation 350 in FIG. 3 and produce air quality measurement information of the electronic device 201 based on the first sensor value having the corrected interval in which the movement continues.

Figure 6:
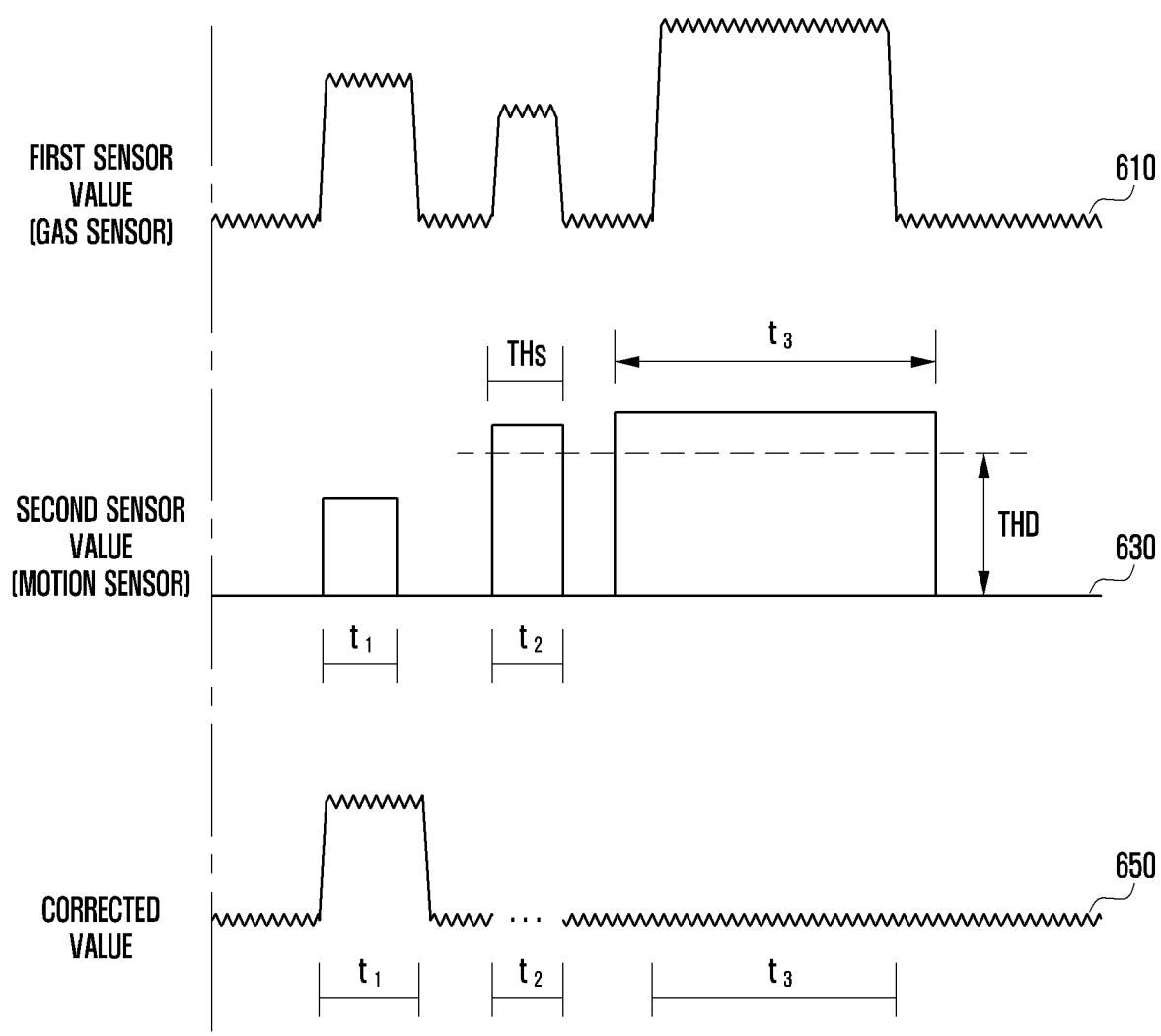
FIG. 6 illustrates the amount of change in sensor values measured by an electronic device according to an embodiment of the disclosure.

FIG. 6 illustrates the amount of change in sensor values measured by an electronic device according to an embodiment of the disclosure.

Referring to FIG. 6, the electronic device (for example, 201 in FIG. 2) according to an embodiment of the disclosure may acquire a second sensor value 630 via a gas sensor (for example, 240 in FIG. 2) and a motion sensor (for example, 260 in FIG. 2), may correct a first sensor value 610 according to whether or not the electronic device 201 makes a movement, which is detected based on the second sensor value 630, and may produce air quality measurement information by using the resulting corrected value 650. In the diagram, 610 refers to the amount of change in the first sensor value measured from the gas sensor 240 according to the flow of time; 630 refers to the amount of change in the second sensor value measured from the motion sensor 260 according to the flow of time; and 650 refers to the amount of change in the corrected value obtained by correcting the first sensor value in view of the movement state of the electronic device 201 determined based on the second sensor value according to the flow of time.

For example, the electronic device 201 may determine whether or not the movement of the electronic device 201 satisfies a designated condition while monitoring the gas sensor 240. The electronic device 201 may identify intervals t1, t2, and t3 in which the movement is continuous, based on the second sensor value 360 measured from the motion sensor 260.

In the case of interval t1 in 630, the second sensor value is less than the movement threshold value THD. Accordingly, the electronic device 201 may make no correction, and may control the first sensor value acquired from the gas sensor 240 to be used as a value for gas measurement (for example, corrected value). It may be understood that, if the second sensor value is below the movement threshold value, the degree of movement is relatively low, and the first sensor value measured in interval t1 may be maintained as a data value for air quality measurement, even if a movement occurs in interval t1.

In the case of interval t2 in 630, the second sensor value is equal to/larger than the movement threshold value THD, but satisfies the condition in which the same moves below the threshold time value THs. Accordingly, the electronic device 201 may delete or ignore the first sensor value measured in interval t2 such that the corrected value in interval t3 may not reflect the first sensor value. In the case of interval t3 in 630, the second sensor value is equal to/larger than the movement threshold value THD, and the electronic device 201 may accordingly correct the first sensor value measured from the gas sensor 240 during the interval t3 in which the movement continues. Consequently, the electronic device 201 may correct the first sensor value in 610 to the corrected value in 650. For example, interval t3 corresponds to a state in which the degree of movement is relatively high, and this increases the possibility that the first sensor value measured from the gas sensor will have an error. Accordingly, the electronic device 201 may correct the first sensor value measured in interval t2. For example, the electronic device 201 may correct the same by replacing the same with a first sensor value measured adjacent to interval t3. Alternatively, the electronic device 201 may receive a gas sensor value measured at the time of interval t3 from another electronic device (for example, electronic device 102 or 197 or server 108 in FIG. 1) and substitute the same for the first sensor value, thereby correcting the same.

The electronic device 201 may produce air quality measurement information based on the corrected value 650 of the gas sensor and may provide the user with the produced ambient air quality measurement information, or may transmit the produced ambient air quality measurement information to another electronic device 102, 108, or 197.

Figure 7:
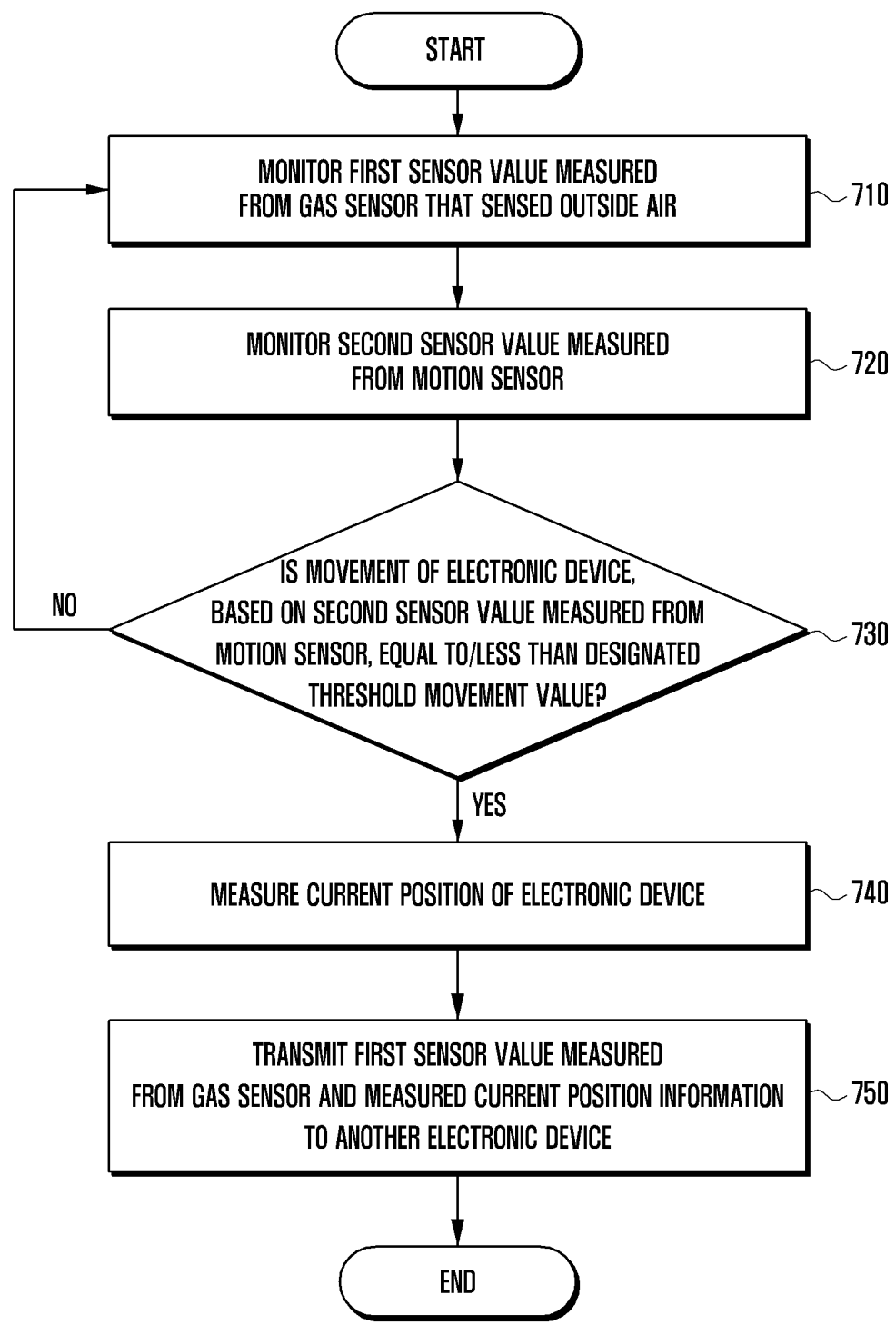
FIG. 7 illustrates a method for measuring a gas by an electronic device having a gas sensor according to an embodiment of the disclosure

FIG. 7 illustrates a method for measuring a gas by an electronic device having a gas sensor according to an embodiment of the disclosure.

Referring to FIG. 7, the processor (for example, processor 120 in FIG. 1 or processor 220 in FIG. 2) of the electronic device 201 according to an embodiment of the disclosure may monitor a first sensor value measured from a gas sensor 240 that sensed ambient air in operation 710. In operation 720, the processor may monitor a second sensor value measured from a motion sensor 260.

In operation 730, the processor 120 or 220 may determine whether or not the movement of the electronic device 201 satisfies a designated condition while monitoring the second sensor value measured from the motion sensor 260. The processor 120 or 220 may determine whether the electronic device 201 is in a stationary state or in a movement state, based on the second sensor value measured from the motion sensor 260.

According to an embodiment, the processor 120 or 220 may determine the movement state based on at least one of a threshold movement value and a threshold time value regarding a movement, which are designated for the second sensor value received from the motion sensor 260. For example, the processor 120 or 220 may determine, as a result of comparing the second sensor value with the threshold movement value, that the electronic device 201 is in a movement state if the second sensor value is equal to/larger than the threshold movement value, and may determine that the electronic device 201 is in a stationary state if the second sensor value is less than the threshold movement value. As another example, the processor 120 or 220 may determine that the electronic device 201 is in a movement state if the amount of change in the second sensor value exceeding the threshold movement value is maintained for a threshold time value or longer, and may determine that the electronic device is in a stationary state if amount of change in the second sensor value does not exceed the threshold time value.

According to another embodiment, the processor 120 or 220 may perform operation 730 after the satisfying the condition that the amount of change in the first sensor value will exceed a threshold value while monitoring the first sensor value measured from the gas sensor, or that the interval in which the first sensor value changes for a designated time is maintained for a threshold time value or longer.

In operation 740, the processor 120 or 220 may measure the current position of the electronic device 201, if the condition that the movement of the electronic device 201 will be equal to/smaller than a designated threshold value, based on the second sensor value measured from the motion sensor 260, is satisfied. For example, the processor 120 or 220 may acquire position information by using the communication module 190. For example, the processor 120 or 220 may calculate the position by measuring the time and distance via the GNSS module. The GNSS module may acquire time information in addition to the position of latitude, longitude, and latitude, and three-dimensional speed information.

In operation 750, the processor 120 or 220 may transmit at least one of the first sensor value measured from the gas sensor 240 and the measured current position information to another electronic device (for example, electronic device 102 or 197 or server 108 in FIG. 1). For example, another electronic device 102, 108, or 197 may be an ambient device included within a configured distance or range from the position thereof, or a server device that manages air quality information in an integrated manner, but is not limited thereto.

For example, the server device (for example, 108 in FIG. 1) that manages air quality information in an integrated manner may store information received from multiple electronic devices (for example, current position information and air quality measurement information), may manage the same in an integrated manner, and, if the electronic device 201 requests air quality sensor value information, may provide the corresponding air quality sensor value with reference to the position of electronic devices communicating with the server device 108.

The electronic device 201 according to an embodiment of the disclosure may assign respective tasks so as to simultaneously or successively perform an operation of correcting the first sensor value received from the gas sensor 240 as in FIG. 3 or transmitting the measured first sensor value and the current position information to another electronic device 102, 108, or 197 as in FIG. 7, if the movement state of the electronic device 201 satisfies a designated condition, based on a second sensor value measured from the motion sensor 260, while monitoring the gas sensor 240, but is not limited thereto.

Figure 8:
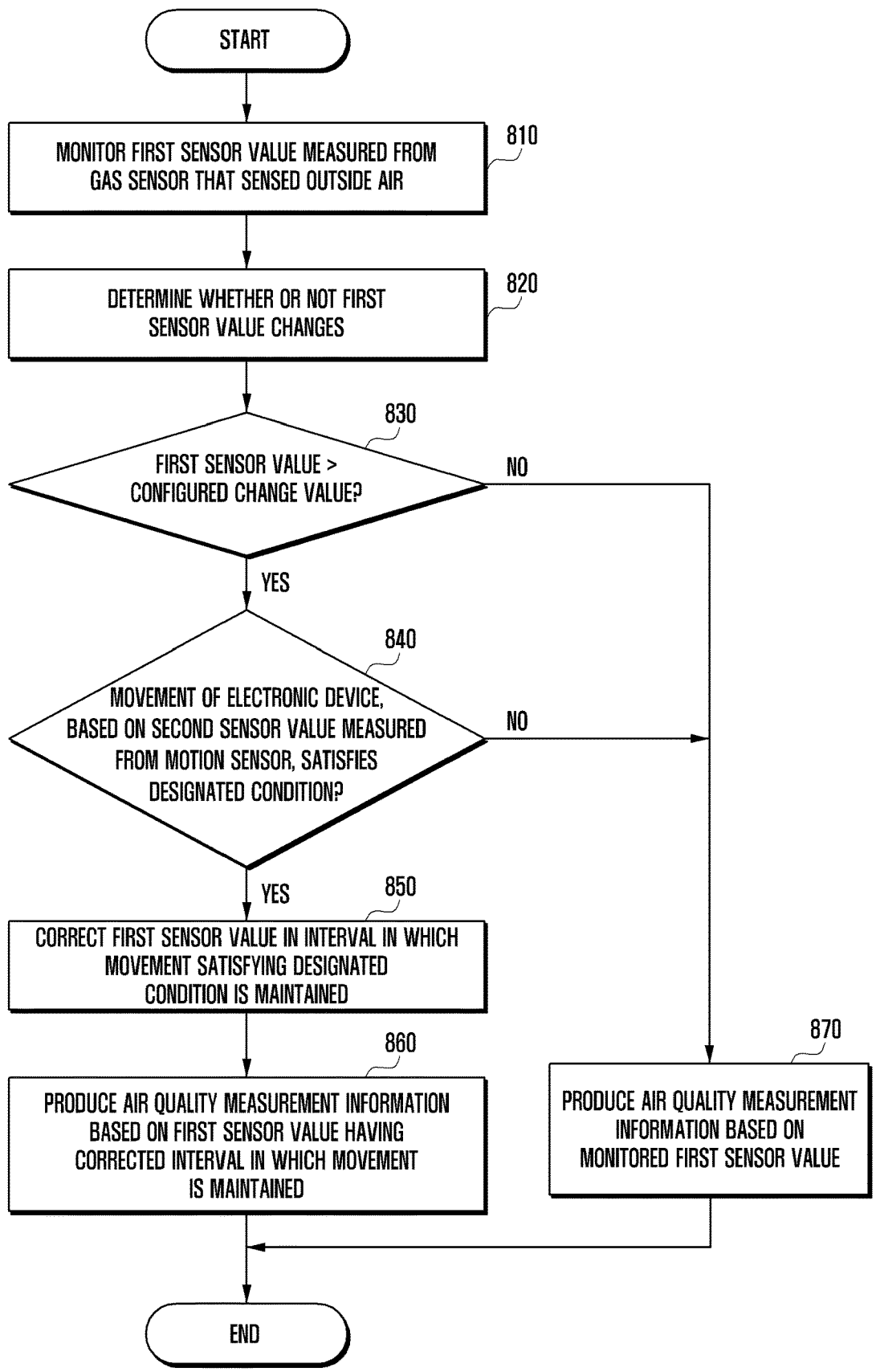
FIG. 8 illustrates a method for measuring a gas by an electronic device having a gas sensor according to an embodiment of the disclosure.

FIG. 8 illustrates a method for measuring a gas by an electronic device having a gas sensor according to an embodiment of the disclosure.

Referring to FIG. 8, the processor (for example, processor 120 in FIG. 1 or processor 220 in FIG. 2) of the electronic device 201 according to an embodiment of the disclosure may monitor a first sensor value measured by a gas sensor that sensed ambient air in operation 810.

In operation 820, the processor 120 or 220 may determine whether or not the first sensor value changes during monitoring. If it is determined in operation 830 that the first sensor value has changed and become equal to/larger than a designated change value, the processor 120 or 220 may proceed to operation 840 and determine, based on a second sensor value received from the motion sensor 260, whether or not the movement of the electronic device 201 satisfies a designated condition. If it is determined that the first sensor value has changed and become less than the designated change value, the processor 120 or 220 may proceed to operation 870 and produce air quality measurement information based on the monitored first sensor value.

In operation 850, if the movement of the electronic device 201 satisfies the designated condition, based on the second sensor value, the processor 120 or 220 may identify a interval (for example, interval t) in which a movement satisfying the designated condition continues, and may correct the first sensor value in the interval in which the movement continues.

The electronic device 201 according to an embodiment may ignore or delete data of the first sensor value produced in the interval in which the movement continues such that data in the interval in which the movement continues is not used to produce air quality measurement information. The electronic device 201 may delete data of the first sensor value produced in the interval in which the movement satisfying the designated condition continues, and may correct the first sensor value in the interval in which the movement continues by using preceding/following data adjacent to the interval in which the movement continues according to the flow of time. Alternatively, the electronic device 201 may replace the first sensor value measured in the interval in which the movement continues with a data value of a gas sensor received from another electronic device (for example, electronic device 102 or 197 or server 108 in FIG. 1), thereby correcting the same.

In operation 860, the processor 120 or 220 may produce air quality measurement information based on the first sensor value having the corrected interval in which the movement continues. Thereafter, the processor 120 or 220 may simultaneously or selectively perform an operation of providing, as a notification, the produced air quality measurement information via the display (for example, display device 160 in FIG. 1) or the audio module (for example, sound output device 155 (for example, speaker) in FIG. 1) or transmitting the same to another electronic device.

If the first sensor value has changed and become equal to/larger than the configured change value, and if the movement of the electronic device 201 does not satisfy the configured condition in operation 840, the processor 120 or 220 may proceed to operation 870 and may produce air quality measurement information based on the monitored first sensor value. Although not illustrated in the drawings, the processor 120 or 220 may additionally provide the user with information regarding whether the current air quality corresponds to a normal state or a contaminated state, based on the produced air quality measurement information.

Figure 9:
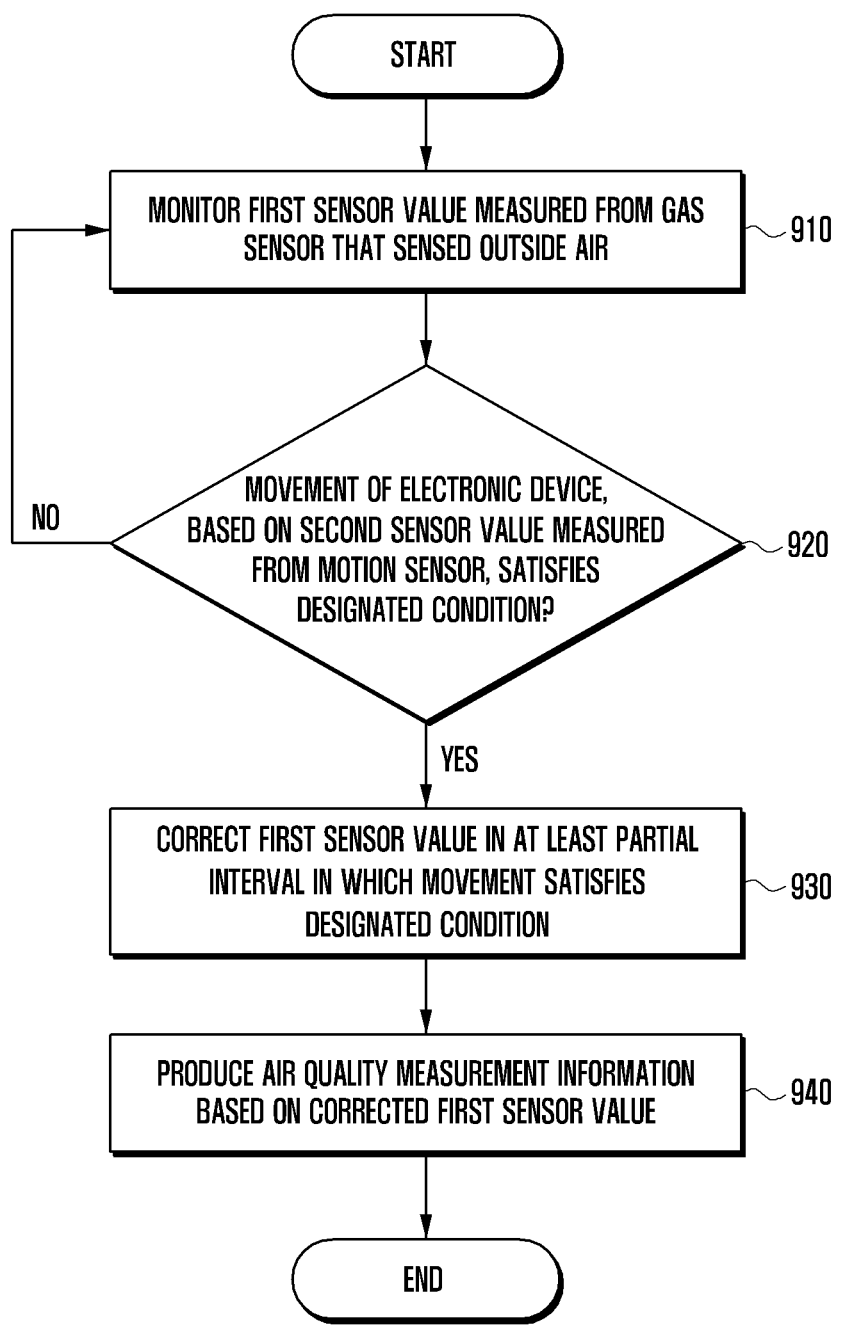
FIG. 9 illustrates a method for measuring a gas by an electronic device having a gas sensor according to an embodiment of the disclosure.

FIG. 9 illustrates a method for measuring a gas by an electronic device having a gas sensor according to an embodiment of the disclosure.

Referring to FIG. 9, the processor (for example, processor 120 in FIG. 1 or processor 220 in FIG. 2) of the electronic device 201 according to an embodiment of the disclosure may monitor a first sensor value measured from a gas sensor 240 that sensed ambient air in operation 910.

In operation 920, the processor 120 or 220 may determine, based on a second sensor value measured from a motion sensor 260, whether or not the movement of the electronic device 201 satisfies a designated condition, while monitoring the first sensor value.

In operation 930, the processor 120 or 220 may correct the first sensor value in at least a partial interval in which the movement satisfies the designated condition.

The processor 120 or 220 according to an embodiment may correct the first sensor value by performing at least one of an operation of ignoring or deleting data of the first sensor value produced in the interval in which a movement satisfying the designated condition continues, an operation of deleting data of the first sensor value produced in the interval in which a movement satisfying the designated condition continues and substituting data preceding/following the interval in which the movement continues according to the flow of time for the first sensor value in the interval in which the movement continues, and an operation of replacing data of the first sensor value produced in the interval in which a movement satisfying the designated condition continues with a data value of the gas sensor 240 received from another electronic device (for example, electronic device 102 or 197 or server 108 in FIG. 1).

In operation 940, the processor 120 or 220 may produce air quality measurement information based on the corrected first sensor value.

Although not illustrated in the drawings, the processor 120 or 220 may perform an operation of identifying the air level by using the produced air quality measurement information and providing information regarding the air level, as a notification, to the user via the display (for example, display device 160 in FIG. 1) or the audio module (for example, sound output device 155 (for example, speaker) in FIG. 1) or transmitting the same to an external electronic device.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device comprising:
   a communication module;
   a gas sensor;
   a motion sensor; and
   a processor, wherein the processor is configured to:
acquire data related to air outside the electronic device by using the gas sensor;
identify a movement of the electronic device by using the motion sensor while acquiring the data,
correct, in case that the movement of the electronic device satisfies a designated condition, at least partial data in an interval in which a movement satisfying the designated condition continues, among the data,
produce information related to quality of the air, based on the data, the at least partial data of which has been corrected,
request an external electronic device to provide another piece of data related to the air corresponding to the interval satisfying the designated condition by using the communication module,
receive the another piece of data from the external electronic device by using the communication module, and
correct the at least partial data by using the another piece of data,
wherein the another piece of data is at least one of data measured by the external electronic device located within a designated range of the electronic device.

2. The electronic device as claimed in claim 1, wherein the processor is configured to:
identify a length of the interval in which the movement satisfies the designated condition; and
ignore the at least partial data, in a case that the length satisfies a designated range, as at least a part of correcting the at least partial data.

3. The electronic device as claimed in claim 1, wherein the processor is configured to:
correct the at least partial data by using another piece of the at least partial data temporally adjacent to the at least partial data, as at least a part of correcting the at least partial data.

4. The electronic device as claimed in claim 1, wherein the another piece of data is at least one of data measured by the external electronic device at a time at which the movement of the electronic device satisfies the designated condition, or data acquired when the movement of the external electronic device is below a designated threshold value.

5. The electronic device as claimed in claim 1, wherein the processor is configured to:
acquire a sensor value that changes according to the movement of the electronic device from the motion sensor; and
determine that the movement of the electronic device satisfies the designated condition in a case that a value satisfying a threshold movement value occurs for a threshold time, at least based on the sensor value.

6. The electronic device as claimed in claim 1, wherein the processor is configured to perform an operation of identifying the movement of the electronic device by using the motion sensor in a case that an amount of change of data acquired from the gas sensor satisfies a designated change value.

7. The electronic device as claimed in claim 1, further comprising:
a display; and
an audio module, wherein
the processor is configured to provide information related to the quality of the air via the display or the audio module.

8. A method for correcting and producing data related to ambient air of an electronic device, the method comprising:
acquiring a first sensor value related to the ambient air of the electronic device from a gas sensor;
identifying a movement of the electronic device based on a second sensor value measured from a motion sensor while acquiring the first sensor value;
correcting, in case that the movement of the electronic device satisfies a designated condition, at least partial data in an interval in which a movement satisfying the designated condition continues, among the first sensor value; and
producing information related to quality of the ambient air, based on the first sensor value, the at least partial data of which has been corrected, wherein correcting the at least partial data of the first sensor value further comprises:
requesting an external electronic device to provide another piece of data related to the ambient air corresponding to the interval satisfying the designated condition;
receiving the another piece of data related to the ambient air from the external electronic device; and
correcting the at least partial data by using the another piece of data,
wherein the another piece of data is at least one of data measured by the external electronic device located within a designated range of the electronic device.

9. The method as claimed in claim 8, wherein, in the correcting of the at least partial data of the first sensor value, a length of the interval in which the movement satisfies the designated condition is identified, and in a case that the movement satisfies a designated range, the at least partial data of the first sensor value produced in the interval in which the movement satisfying the designated condition continues is ignored.

10. The method as claimed in claim 8, wherein, in the correcting of the at least partial data of the first sensor value, data of the first sensor value in the interval in which the movement of the electronic device satisfying the designated condition continues is deleted, and partial data of the first sensor value is replaced by using another piece of the at least partial data temporally adjacent to an interval in which movement is maintained.

11. The method as claimed in claim 8,
wherein the another piece of data is at least one of data measured by the external electronic device at a time at which the movement of the electronic device satisfies the designated condition, or data acquired when the movement of the external electronic device is below a designated threshold value.

12. The method as claimed in claim 8, further comprising:
identifying current position information of the electronic device in a case that the movement of the electronic device satisfies a configured condition; and
transmitting at least one of a first sensor value measured from the gas sensor, a corrected value, of which the at least partial data has been corrected, and the identified current position information, to the external electronic device.

13. The method as claimed in claim 8, wherein, in the identifying of the movement of the electronic device, the movement of the electronic device is identified by using the motion sensor in a case that an amount of change of data acquired from the gas sensor satisfies a designated change value.

* * * * *